United States Patent
Levin et al.

(10) Patent No.: US 6,303,389 B1
(45) Date of Patent: Oct. 16, 2001

(54) RAPID FLOW-THROUGH BINDING ASSAY APPARATUS AND METHOD THEREFOR

(75) Inventors: Andrew E. Levin, Wellesley; William Bowers, Cambridge, both of MA (US)

(73) Assignee: Immunetics, Cambridge, MA (US)

( * ) Notice: Subject to any disclaimer, the term of this patent is extended or adjusted under 35 U.S.C. 154(b) by 0 days.

(21) Appl. No.: 09/106,824

(22) Filed: Jun. 29, 1998

Related U.S. Application Data

(63) Continuation-in-part of application No. 09/045,630, filed on Mar. 19, 1998, which is a continuation-in-part of application No. 08/939,778, filed on Sep. 29, 1997, which is a continuation-in-part of application No. 08/884,017, filed on Jun. 27, 1997, now abandoned.

(51) Int. Cl.[7] ................................................. G01N 33/533
(52) U.S. Cl. ........................ 436/518; 436/177; 436/809; 435/7.1; 435/7.94; 435/287.7; 435/287.8; 435/288.2; 435/288.3; 435/288.4; 422/56; 422/57; 422/58; 422/99; 422/102; 422/101
(58) Field of Search ........................ 422/56–58, 99.102, 422/101; 435/7.1, 7.94, 287.7, 287.8, 288.2, 288.3, 288.4; 436/518, 177, 809; 206/233

(56) References Cited

U.S. PATENT DOCUMENTS

| | | |
|---|---|---|
| 4,493,815 | 1/1985 | Fernwood et al. ................... 422/101 |
| 4,713,349 | 12/1987 | Levin ................................. 436/515 |
| 4,754,656 * | 7/1988 | Charm . |
| 4,834,946 | 5/1989 | Levin ................................. 422/101 |
| 4,912,034 | 3/1990 | Kaira et al. . |
| 4,948,442 | 8/1990 | Manns .............................. 156/73.01 |
| 4,978,507 | 12/1990 | Levin ................................. 422/100 |
| 5,047,215 | 9/1991 | Manns ................................ 422/101 |
| 5,087,556 | 2/1992 | Ertinghausen . |
| 5,100,626 | 3/1992 | Levin ................................. 422/100 |
| 5,208,161 | 5/1993 | Saunders . |
| 5,219,421 * | 6/1993 | Tipping . |
| 5,227,137 | 7/1993 | Monti et al. ........................ 422/101 |
| 5,540,354 * | 7/1996 | Annand . |

FOREIGN PATENT DOCUMENTS

WO 88 06723   9/1988  (WO) .

OTHER PUBLICATIONS

The Fisher Catalog, p. 123, (1990).
Promotional Material, "The three–in–one System for Dot/Slot Blotting or DNA / RNA Transfers from Min Gels in 30 Minutes!", American Bionetics ( 4 pages).
Promotional Material, "The Convertible™ Filtration Manifold System", GIBCO BRL, 5 pages (1991).
Promotional Material, The Fast Blot–Developer™ System, Pierce Chemical Company, pp. 20–21.
Promotional Material, "Fast Blot–Developer™ System, For Use with Full Size Gels," Pierce Chemical Company (1995), pp. 1–9.

(List continued on next page.)

*Primary Examiner*—Christopher L. Chin
*Assistant Examiner*—Bao-Thuy Nguyen
(74) *Attorney, Agent, or Firm*—Foley, Hoag & Eliot LLP

(57) ABSTRACT

The invention includes assay cassettes that can be employed during rapid flow-through binding assays. The assay cassettes can be disposable units suitable for one-time use and readily assembled to include a filter membrane carried between an upper plate and a lower plate. A pattern of channels can extend through the top plate to allow a fluid sample to be applied through the top plate and onto the filter. The bottom plate can include a plurality of channels that are aligned with the channel of the top plate and which will allow a negative pressure to be applied to the underside of the filter membrane to draw the sample through the filter. In one embodiment, the cassette includes a frangible section that allows the cassette to be divided into a first and second component.

16 Claims, 11 Drawing Sheets

OTHER PUBLICATIONS

Promotional Material, "Labware & Equipment," Pierce Chemical Company (O–188–O–189).

Promotional Material, "Immunoassays," Pierce Chemical Company (T–310–T–311).

Promotional Material, "Instruction–Fast Blot Developer," Pierce Chemical Company, 10 pages (1991).

Promotional Material, "Immunetics introduces. . . Miniblotter® and Minislot™ Instruments for Checkerboard DNA Hybridization and Checkerboard Antibody Blots," Immunetics (2 pages).

Socransky, S.S. et al., "Checkerboard DNA–DNA Hybridization," Biotechniques 17 (4): 788–791 (1994).

Promotional Material, "The Multi screen Assay System," Millipore (pp. 399–403 & 477–479).

Towbin, H., et al., "Electrophoretic Transfer of proteins from polyacrylamide gels to nitrocellulose sheets: Procedure and some applications", Proc. Natl. Acad. Sci. USA, vol. 76, No. 9, pp. 4350–4354 (Sep. 1979).

* cited by examiner

RAPID FLOW-THROUGH BINDING ASSAY APPARATUS AND METHOD THEREFOR

REFERENCE TO RELATED APPLICATIONS

This application is a continuation-in-part of to U.S. Ser. No. 08/884,017, filed Jun. 27, 1997, now abandoned entitled RAPID FLOW-THROUGH BINDING ASSAY APPARATUS AND METHOD, and naming as inventor in the present application, Andrew E. Levin U.S. Ser. No. 08/939,778, filed Sep. 29, 1997, entitled RAPID FLOW-THROUGH BINDING ASSAY APPARATUS AND METHOD, naming as inventor in the present application, Andrew E. Levin, and U.S. Ser. No. 09/045,630, filed Mar. 19, 1998, entitled SYSTEMS AND METHODS FOR RAPID BLOT SCREENING, naming as inventor in the present application, Andrew E. Levin all of which are herein incorporated by reference.

FIELD OF THE INVENTION

The invention relates generally to improved devices for performing binding assays and, more particularly, to rapid flow-through binding assay apparatus and methods.

BACKGROUND OF THE INVENTION

Binding assays are routinely used to screen for and diagnose a host of diseases and conditions, including Lyme disease, herpes, acquired immunodeficiency syndrome (AIDS), streptococcal infections, lupus and pregnancy. Such assays are relatively simple in theory, utilizing the binding affinity between two or more binding members to detect and/or quantify the presence of one of the members, referred to herein as the analyte. Binding members comprise a wide range of substances, including antigens, antibodies, haptens, complimentary nucleic acid sequences, ligands, small molecules and receptors. Antigen-antibody binding member pairs used in immunoassays currently enjoy the most widespread use.

A common format of a binding assay involves immobilizing a binding member specific for the analyte on a paper-like sheet or membrane. The membrane is then contacted with the test sample and appropriate reagents under conditions allowing binding to occur between the immobilized binding member and any analyte in the sample, with means for detecting binding events also provided. Often a labeled second binding member which binds to the first binding member-analyte complex is added to provide a detectable signal on the membrane.

The sandwich immunoassay is an example of one commonly used binding assay for antibody detection. In a generic sandwich immunoassay, the antigen is immobilized on a solid substrate. Antibody containing solution, e.g., diluted serum, is incubated with the immobilized antigen. Antibodies specific to the antigen bind to it, and unbound antibodies are then removed by buffer washes. A detection agent which may typically be a secondary antibody conjugated to an enzyme, is then incubated with the primary antibody-antigen complex. Finally, an enzyme substrate is added which is converted into a visual, detectable product whenever the enzyme is. Such multi-step sandwich immunoassays can be developed in many different ways depending on assay requirements.

A Western Blot is another example of a commonly used immunoassay. In current practice, the Western Blot method comprises a sequence of incubation and wash steps performed on a membrane bearing electrophoretically resolved antigen bands. Typically, the membrane is cut into narrow strips, each bearing the identical pattern of antigen bands. Strips are then processed in reagent solutions individually in narrow trays, each typically holding 0.5–2.0 ml. In the first step, the strip is incubated with a blocking solution containing a non-specific protein, e.g., non-fat dry milk, bovine serum albumin, newborn calf serum or gelatin. After washing off excess blocking solution with a wash buffer, typically a physiological saline buffer containing a low percentage of detergent, the strip is then incubated with antibody solution. Antibody solution may be diluted human or animal serum, cerebrospinal fluid, dried blood spot eluate, monoclonal antibody, to name a few. Unbound antibody is then washed off with buffer, and the strip is incubated in the detection reagent. In a typical application, the detection reagent could be goat-anti-human IgG-alkaline phosphatase conjugate. Unbound detection reagent is washed off with buffer, and finally the substrate (for alkaline phosphatase, a common substrate is 5-bromo-4-chloro-3-indolyl phosphate plus nitroblue tetrazolium) for the detection enzyme is added. The conversion of the substrate to a visually detectable product is allowed to proceed until optimal visualization of bands, and then substrate is washed away. The strip is typically dried, providing a permanent record of the assay result. Bands on the strip indicating antibody reactivity can be compared with control strips to determine the specificity of the immunoreaction. In currently used algorithms for HIV and Lyme testing, a positive test result is defined as the appearance of certain combinations of specific bands. For example, an HIV Western Blot test requires the presence of two bands to be considered positive, while a Lyme Western Blot test requires five out of ten bands to be positive for IgG, or two out of three bands to be positive for IgM.

As described above, the Western Blot method involves incubating the membrane strips sequentially in reagent solutions usually contained in a tray. In typical protocols, incubations with antibody solutions and detection reagents may take 30 minutes to several hours each. Wash steps may take 5–10 minutes each. The total time for processing a blot is therefore, not less than one hour, and is often several hours.

It would thus be desirable to provide a method and apparatus for the rapid processing of a binding assay, e.g., an immunoassay, including a Western Blot.

SUMMARY OF THE INVENTION

The invention includes, inter alia, systems and methods for providing assay cassettes that can be employed during rapid flow-through binding assays. The assay cassettes can be disposable units suitable for one-time use and readily assembled to include a filter membrane carried between an upper plate and a lower plate. A pattern of channels can extend through the top plate to allow a fluid sample to be applied through the top plate and onto the filter. The bottom plate can include a plurality of channels that are aligned with the channel of the top plate and which will allow a negative pressure to be applied to the underside of the filter membrane to draw the sample through the filter. In one embodiment, the cassette includes a frangible section that allows the cassette to be divided into at least a first and second component.

More specifically, in one embodiment, the cassettes comprise a multi-channeled top plate that can be received into a multi-channeled bottom plate to define an interior chamber between the top plate and the bottom plate. A membrane having antibodies bound thereon can be received within the interior chamber and sandwiched between the top plate and bottom plate. To this end, the bottom plate and top plate can include an engagement mechanism, such as a notch and catch assembly that allows the top plate and bottom plate to be joined together. The bottom plate and top plate can be joined together in such a manner that a membrane placed into the interior chamber of the cassette is sandwiched between the bottom surface of the top plate and the top surface of the bottom plate. The assembled cassette with the membrane therein can be placed in an assay machine, such as a machine of the type described in U.S. Ser. No. 09/045, 630, filed Mar. 19, 1998, entitled SYSTEMS AND METHODS FOR RAPID BLOT SCREENING. As disclosed therein the cassette can be compressed by the plates of a container that can compress together the top plate and bottom plate of the assay cassette to hold together the top plate and bottom plate with sufficient force that a series of substantially tight seals are formed around the portions of a filter membrane, sandwiched between the two plates, that are enclosed by the walls of the channels found in the top plate. Effectively, this causes the filter membrane to act as a series of strips of membrane wherein each strip is isolated from the other strips formed on the membrane by the grooves of the upper plate. In this way, the assay cassette can be employed for carrying out a plurality of reactions with reduced or eliminated cross-contamination.

In one embodiment the invention assay cassettes described herein, comprise a top plate having a frangible portion extending transversely across the top plate and a bottom plate having a peripheral side wall and being adapted to couple with said top plate to define an interior chamber capable of receiving a filter membrane. In one embodiment, the frangible portion is formed by a score extending across the width of the top plate. However, in other embodiments the frangible portion can include a cavity or a frangible seal or any other mechanism suitable for allowing the top plate to be divided into separate components. Alternatively, the top plate can include a hinge for allowing the assay cassette to be swung open for giving access to the filter membrane stored therein. The assay cassette can include a top plate that has a recessed bottom surface which extends into a chamber a distance sufficient to butt against a membrane received therein. The top plate can also include a substantially open channel that extends through the top plate and provides an opening through the top plate to allow contact with a membrane within the chamber. Accordingly, the assay cassette can include open channels that allows a sample material to be delivered through an opening in the top plate and onto a membrane contained within the chamber of the assay cassette. The open channels can be formed in a pattern, such as a plurality of longitudinally extending channels, or as a plurality of concentric rings. However, it will be understood that any suitable pattern can be employed without departing from the scope of the invention, including systems with two, four, eight, or twenty-four channels, or openings formed as dots, ellipses, wells or any other suitable configuration.

In a further embodiment, it is understood that the assay cassette includes an engagement mechanism for holding the top plate together with the bottom plate. In one embodiment, the engagement mechanism includes a catch for holding the top plate together with the bottom plate. Optionally, the engagement mechanism allows for some vertical movement of the plates relative to each other. Accordingly, the top plate and bottom plate, in an engaged state, can be moved closer together, sandwich a filter membrane therebetween. The catch can be formed from a recessed surface in the top plate which will slidingly receive and engage with a surface protrusion located on the side wall of the bottom plate. Alternatively, the engagement mechanism can include a clasp capable of joining the top plate together with the bottom plate. In this embodiment, the clasp can be a simple elastic element, such as a rubber band that can be fitted on the outside of the cassette when the top plate and bottom plate are joined together. Other mechanisms for joining and holding together the top plate and bottom plate can be practiced without departing from the scope of the invention.

In a further embodiment, the assay cassette can include a vacuum port disposed in the bottom plate. The vacuum port can allow a vacuum to be applied to the interior chamber, and is understood to facilitate drawing fluid through the filter membrane. In one embodiment, the vacuum port is formed in part by channels formed in the bottom plate of the cassette assembly. In a preferred practice, the channels in the bottom plate are aligned with the channels in the top plate to provide for fluid to be drawn through the channels in the top plate, and the membrane and into the channels of the bottom plate, where any excess fluid can be drawn off to a waste container.

In one practice the assay cassette, when assembled, is put into a container that is part of an agitator system for performing rapid flow-through assays. One such system provides a vacuum port that may be operatively-linked to a vacuum source. Test samples and assay reagents may be applied to the filter membrane of the assay cassette through the opening in the top plate and the vacuum source can apply a negative pressure to the channels bottom plate to draw material and reagents through the membrane.

Additionally, the systems described herein can include systems for opening an assay cassette having a frangible section. These systems can include a base plate, and a top plate that is hingedly mounted to the base plate and spaced away from the base plate for defining a gap capable of receiving one end of the assay cassette. Once the assay cassette is received within the device, pivoting the top plate relative to the base plate provides a shearing force capable of opening the assay cassette. Accordingly, it will be understood that the assay cassettes described herein can be opened in response to a shear force applied to the frangible section, wherein in one embodiment the assay cassette opens by having the frangible section of the assay cassette break-off and separate from the cassette, or alternatively, the frangible section can break along one side of the assay cassette, with the other side still attached, yet in manner that allows the two sections to move relative to each other to provide access to the interior of the cassette.

It will be appreciated that the membranes of the invention may be prepared by methods known to those skilled in the art. For example, antigens may be applied to the membranes by electrophoresis and transblotting. Antigens or other binding members may also be applied directly to membranes by, for example, pens, brushes, spray devices, ink jet devices as well as flow-through devices such as the Minislot™ (Immunetics, Cambridge, Mass. ). It will also be appreciated that the plates and other portions of the apparatus may be made by methods known in the art, and are preferably of a solution-resistant material, e.g., Plexiglas, molded plastics, aluminum, stainless steel or other synthetic materials.

Generally, according to a method of the invention, a test sample is allowed to come into contact with the surface of the membrane (on which a binding member specific for an analyte of interest is immobilized), through a multiple-channeled plate of a removable cassette of the invention. Appropriate volumes of test samples and assay reagents are placed, e.g., by pipetting, on the membrane through the channels. The test sample is drawn through the membrane under vacuum. The channels may then be flushed to rinse away unbound materials. It will be appreciated that additional reagents, indicators, or binding members can also be introduced into the channels, preferably under vacuum, to provide a detectable signal. If the test sample contains an analyte of interest, it will bind to the binding member specific for the analyte on the membrane.

The removable cassettes described herein can be provided to the consumer for a single and disposable use. The membrane provided can include any desired binding members for detection of analytes of interest, including several different binding members, to permit simultaneous screening or the presence of more than one analyte. The membrane may also include only one type of binding member, allowing detection of a desired analyte from several test samples. The methods of the invention may also require smaller volumes of reagents than known methods and thus the apparatus and methods of the invention may provide additional costs savings. A further advantage of the apparatus and methods of the invention is the increased speed of assay as compared to conventional assay apparatus and methods. Yet a further advantage of the apparatus and methods of the invention is the increased clarity of the visual result as compared to conventional apparatus and methods.

The invention also provides kits comprising a removable cassette having a membrane with preselected binding members specific for analytes of interest immobilized thereon, and reagents for carrying out the specific binding assay. The kit may further comprise instructions for use as well as appropriate packaging.

BRIEF DESCRIPTION OF THE DRAWINGS

The foregoing and other objects and advantages of the invention will be appreciated more fully from the following further description thereof, with reference to the accompanying drawings wherein.

DETAILED DESCRIPTION OF THE ILLUSTRATED EMBODIMENTS

Figure 1:
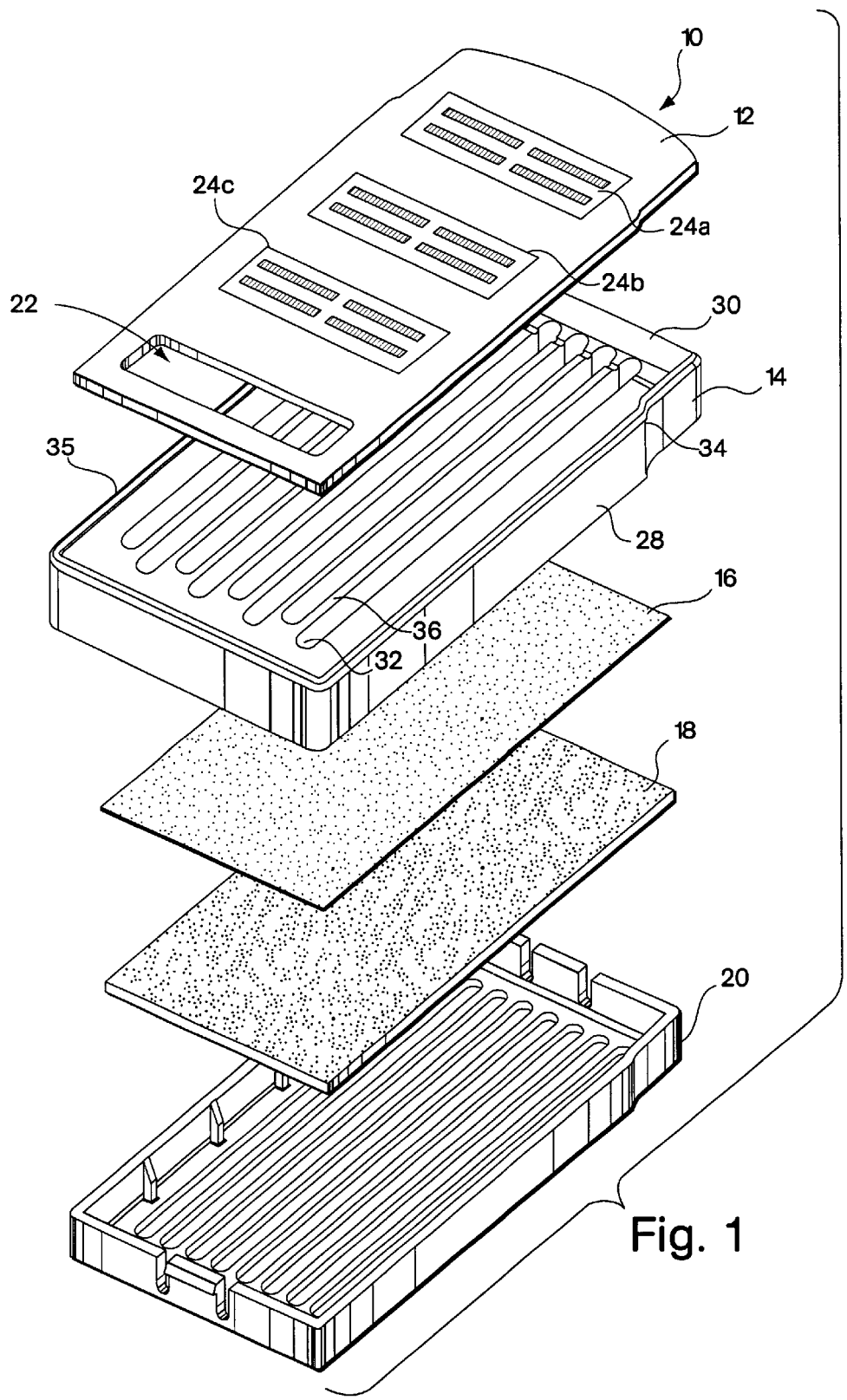
FIG. 1 provides an exploded view of one assay cassette according to the invention.

To provide an overall understanding of the invention, certain illustrative embodiments will now be described, including an assay cassette for use during rapid flow-through assaying, that includes a frangible section. However, it will be understood by one of ordinary skill in the art that the assay cassettes described herein can be adapted and modified to provide systems that can be employed in other types of assays, including any assay that requires filtering a sample material through a filter membrane, such as direct or sandwich assays.

In such assays, an analyte is bound to a binding member immobilized on the membrane, and a labeled second binding member is bound thereto to provide a detectable signal. Any variety of labels or indicator schemes which provide a detectable signal that analyte binding has occurred can be employed with the systems described herein, including, for example, direct labels such as fluorescent, radioactive and chromophoric labels. Labels which may require development or enzymatic reagents, such as horseradish peroxidase or alkaline phosphatase, can also be utilized. Additionally, indirect label vehicles such as Protein A or avidin/biotin methods, know to those skilled in the art, can also be adapted for use with the apparatus and methods described herein. Accordingly, will be understood that the systems and methods described herein are exemplary and provided for purposes of illustrating the invention and that many modifications, substitutions, and additions can be made to the systems described herein without departing from the scope of the invention.

In a typical multi-step binding assay, each reagent or wash solution is added sequentially as soon as the previous solution has been fully aspirated through the membrane. For example, in detecting antibodies reactive with antigens on a Western Blot, the sequence of solutions generally comprises, in order: blocking solution (e.g., detergent Tween-20), primary antibody (diluted human serum), three washes with buffer containing phosphate-buffered saline and Tween-20 detergent, secondary antibody (e.g., diluted anti-human IgG-alkaline phosphatase conjugate), three more buffer washes, distilled water, and enzyme substrate (e.g., 5-bromo-4chloro-3-indoly-phosphate and nitroblue tetrazolium solution). Given the rapidity of aspiration through the membrane, processing with all solutions can be completed in about 10 minutes. This method is thus 10–20 times faster than the conventional processing method.

The assay device and binding assay of the invention are well-suited for conducting immunoassays for the presence of analytes in any biological material, e.g., an antibody or antigen analyte in human or animal serum, urine, stool, saliva or other body fluids, secretions or excretions. It will be appreciated, however, that the device and assays of the invention can be adapted to utilize the binding affinity of any binding member such as, for example, haptens, complimentary nucleic acid sequences, ligands, small molecules and receptors. The invention can also be used to screen for the presence of microbial organisms, including bacteria, viruses and fungi. The device of the invention can additionally be used to screen or otherwise characterize binding specificities of monoclonal antibodies, antibodies of different species and antibodies produced by genetic engineering or other in vitro techniques.

Examples of binding assays which can be conducted with the device and in accordance with the principles of the invention include assays to detect the presence of antibodies specific for bacterial proteins of *Borrelia burgdorferi* which causes Lyme disease, for viral proteins of HSV which causes herpes, for viral HIV proteins implicated in acquired immunodeficiency syndrome (AIDS), for antigens specific to human chorionic gonadotropin (HCG) to detect pregnancy, for rheumatoid arthritis, and for a variety of bacterial and viral infections. It is also contemplated that the device and assays of the invention be used to screen for toxins such as, e.g., that of *Clostridium difficile,* and to screen for specific nucleic acid sequences to detect, e.g., pathogens, genetic defects, etc.

The invention also provides kits comprising a top plate with channels and a membrane with preselected binding members specific for analytes of interest immobilized thereon, and packaging enclosing the top plate and membrane. Appropriate processing reagents for carrying out the specific binding assay may also be included, as well as instructions for use. To initiate the test the operator would need only to connect the disposable unit to a vacuum source and apply test solutions to the channels. Application of test solutions could be performed manually, or by a robotic liquid handling system under software control. In all cases, a visual or otherwise detectable pattern of reactivity, in the form of bands or otherwise, is generated in each test channel, and can be analyzed to obtain a test result.

FIG. 1 depicts one embodiment of a cassette assembly according to the invention. Specifically, FIG. 1 depicts an assay cassette 10, having a label 12, a top plate 14, a membrane 16, a filter pad 18, and a bottom plate 20. The cassette 10 depicted in FIG. 1 is a disposable device, typically manufactured for one-time use and made out of plastic components which are readily manufactured by techniques well known in the art.

The exploded view of FIG. 1 shows the relative order in which the above elements can be assembled together to provide an assay cassette suitable for rapid flow-through binding assays. Specifically, FIG. 1 shows that the label 12 can attach to the top plate 14 and that the top plate 14 can fit over the bottom plate 20 so that the membrane 16 and the filter pad 18 fit within an interior chamber that is formed within the assay cassette 10 when the top plate 14 is fit over the bottom plate 20. Accordingly, the elements depicted in FIG. 1 cooperate to form an assembly that can securely hold a membrane 16 between the two plates of the cassette. Moreover, as explained in greater detail hereinafter, the top plate and bottom plate can be assembled in a manner that allows the plates to be moved closer together, for compressing the membrane 16. This cassette assembly can then be employed within a device for performing a rapid flow-through assay, such as the devices described in the above-referenced U.S. patent application Ser. No. 09/045,630, filed Mar. 19, 1998.

The label 12 depicted in FIG. 1 is a plastic label having a two-part adhesive backing which allows the label 12 to be affixed to the upper surface of the top plate 14. To this end, the underside of the label 12 can have an adhesive material applied around the rim of the label 12 such that the label 12 can seal to the perimeter of the top plate 14. In this embodiment, the adhesive material is away from the channels 32, and therefore away from the sample and reagent materials. The portion of the label 12 that fits over the channels 32 can be water proof, or other wise fluid resistant. In the embodiment of FIG. 1, the label 12 includes a sample/viewing window 22 disposed at one end of the label 12. The sample/viewing window 22 is an aperture extending transversely along one end of the label 12 and providing an aperture through which a sample material can be delivered into the cassette assembly 10. The depicted label 12 includes three peel-away labels 24A–24C. Each of these three labels provides a set of data fields into which a lab technician can enter information. The information can include the patient identifier, such as the patient's name or social security number, the date of performing the assay, a barcode describing information about the assay, patient or lab, or any other relevant information. Each of the three peel-away labels 24A–24C can be employed by the lab technician for labeling different components that are employed during the assay. For example, one label can be left on the cassette device 10, or located to a different location on the cassette device 10. A second label can be maintained in-house, such as in an internal lab notebook. And the third peel-away label can be employed for labeling a kit that includes the processed portions of the assay, such as a processed membrane. The depicted label 12 is waterproof, or otherwise fluid resistant for both top and bottom. In alternate embodiments, the label 12 can be a multi-part label, wherein individual parts of the label can be peeled from the multi-part label and applied to different components of the test kit.

The top plate 14 depicted in FIG. 1 includes a side wall 28 that surrounds the periphery of the plate 14. In the top surface 30 of the top plate 14, there are a plurality of channels 32 that extend longitudinally across the top surface 30. In the depicted embodiment there are eight channels 32, however any number of channels can be employed depending on the application. The label 12 fits between the walls of a raised lip 35 which extends around three sides of the top surface of the top plate 14. The depicted top plate 14 further includes a weakened portion 34 that in the depicted embodiment comprises a score disposed at one end of the top plate 14 and extending for the full width of the top plate 14 and being transverse to the channels 32.

Figure 2:
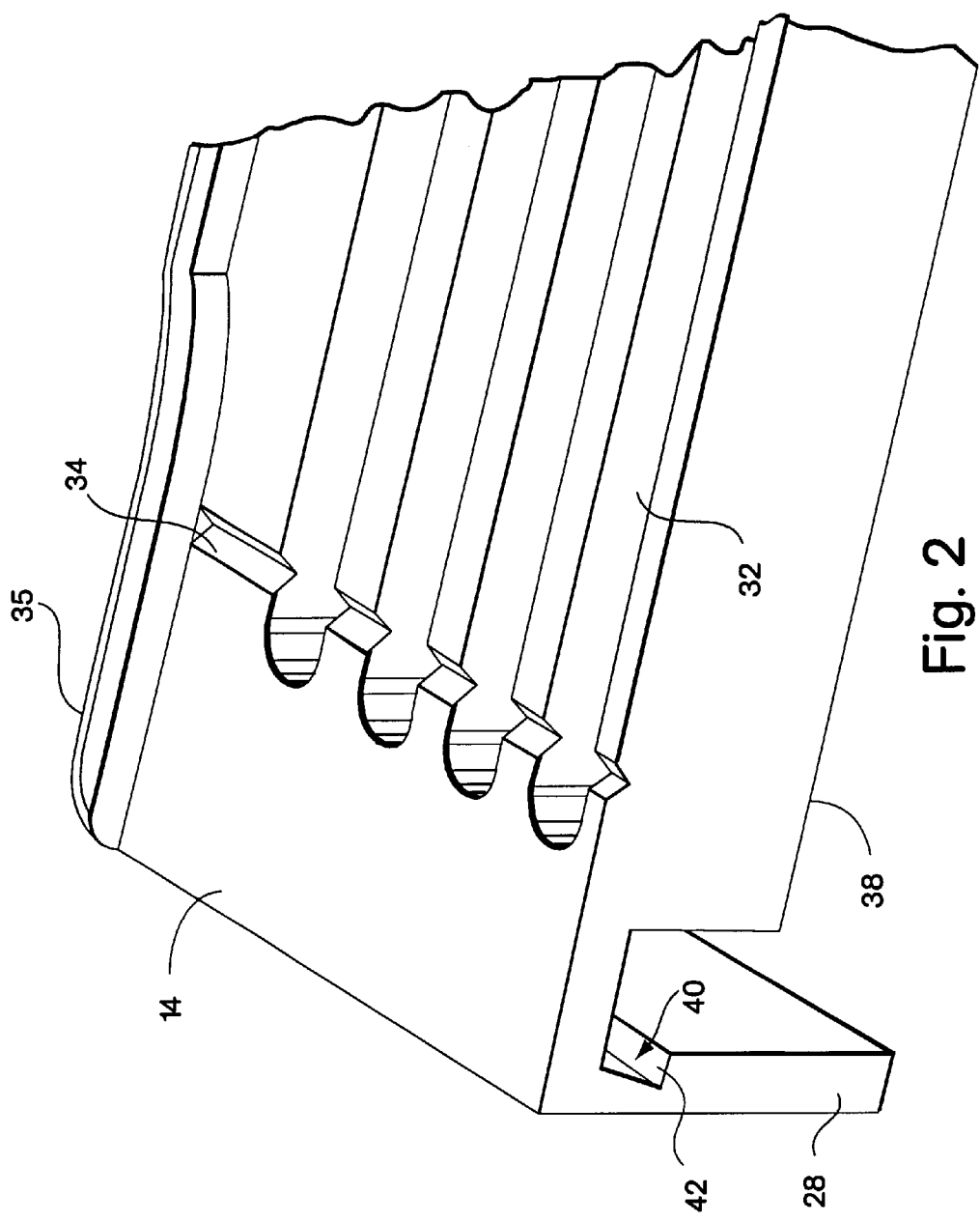
FIG. 2 provides a cross-sectional view of the top plate of the assay cassette of FIG. 1.

FIG. 2 depicts in greater detail a portion of the top plate 14. Specifically, FIG. 2 provides a cut-away view and side perspective of one end of the top plate 14. Specifically, FIG. 2 shows in greater detail the frangible portion 34 that extends transversely across the top of the top plate 14. The cut-away perspective of FIG. 2 shows that the top plate 14 has a recessed bottom wall 38 and has a catch wall 40 that has a plateau 42 that, as will be described in greater detail hereinafter, provides a surface for engaging against a catch on the bottom plate 20 depicted in FIG. 1 to engage the bottom plate 20 with the top plate 14.

FIG. 2 also illustrates in greater detail that the frangible portion 34 is formed as a V-shaped groove that extends partially into the top plate 14. It will be understood that this groove provides a weakened section along the top plate 14 along which a fracture can more easily occur. In particular, it is understood that a mechanical force, such as a shear force applied to the top plate 14 can result in a fracture occurring along the frangible portion 34 such that the fracture travels downward from the grove 34 to the recessed bottom surface 38. This results in the fracture of the top plate 14, fracturing into two components, a larger component and a smaller component. Although in the depicted embodiment, the weakened portion is depicted as a score that extends across the width of the top plate 14. It will be understood that the frangible portion 34 can also include a concavity extending along the width of the top plate 14 wherein a fracture is more easy to occur, a breakable seal that can be pulled away by a lab technician to separate the top plate 14 into a larger component and a smaller component, or any other mechanism suitable for providing a weakened portion within the top plate 14. Other embodiments can include notches that are square, or V-shaped, thin wall molded sections that in molding would provide internally molded knits or stress lines, or any other structure susceptible to breakage. It will further be understood that although the frangible portion 34 is depicted as being in the top surface of the top plate 14 at one end of the top plate 14, it will be understood that the frangible portion 34 can be located at alternative positions, including at the other end of the top plate 14, close to the center of the top plate 14, at an edge of the top of 14 between the wall 14 and the side wall 28, on the underside of the top plate 14, in the side walls, or any other suitable location. In other embodiments, the cassette can be made with clasps that allow a distal end of the assembled cassette to be separated from a proximal end of the cassette, therefore, providing a system wherein a section of the assembled cassette is detachable from the rest of the casette.

Figure 3:
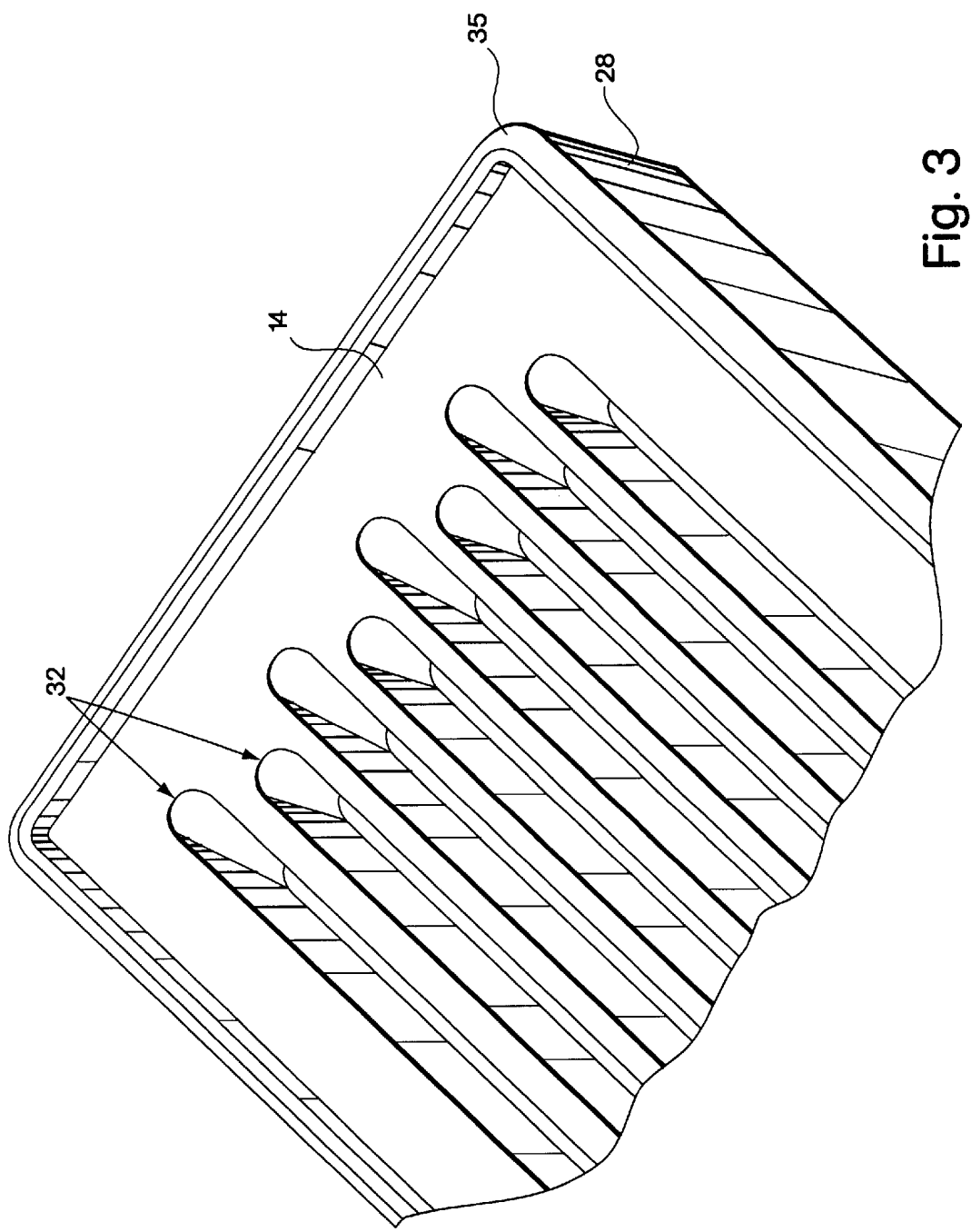
FIG. 3 depicts in greater detail the channels of the top plate of FIG. 2.

With reference to FIG. 3, the channels 32 and the top plate 14 can be described in greater detail. The channels 32 depicted in FIG. 3 are open grooves that extend longitudinally and that provide openings from the top surface 30 of the top plate 14 through to the bottom surface 38 of the top plate 14. Accordingly, the channels 32 provide openings through which a substance can be delivered into the cassette assembly 10. In the depicted embodiment the channels 32 are alternately staggered to provide for greater visibility as the lab technician fills each of the grooves with sample material to be processed during the assay. It will be understood that each of the channels 32 can receive a separate sample of material to be assayed. It will further be understood that the channels 32 are fluidicly isolated from each other such that fluid cannot pass through the walls of the channels 32 to leave one channel and to enter into another channel. It will also be understood that the channels can be provided by other elements, including dots, and wells, similar to the dots found on a micro-titer plate, grooves, transverse channels or combinations thereof.

Figure 4:
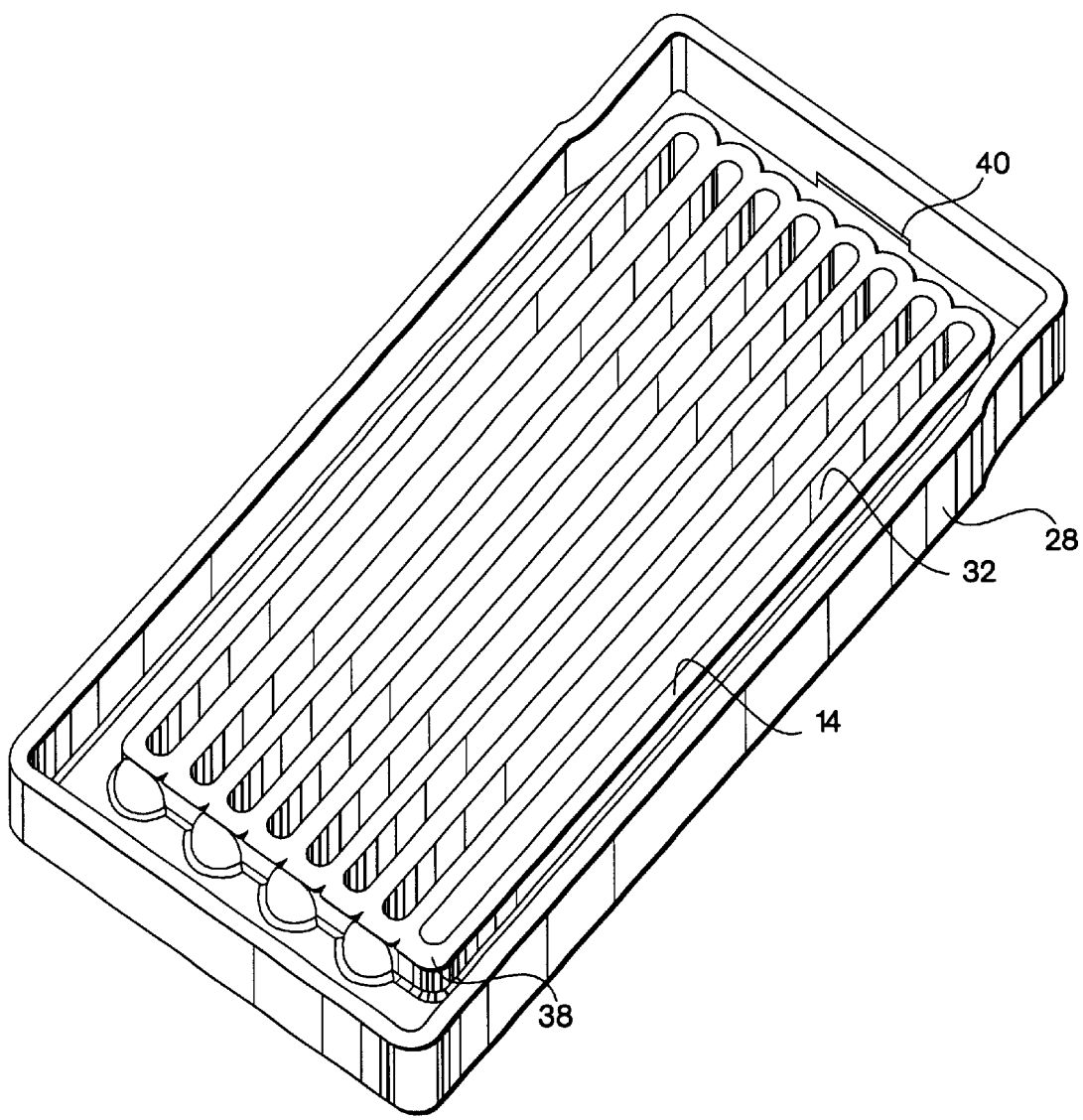
FIG. 4 depicts the underside of the top plate of FIG. 2.

FIG. 4 depicts in greater detail the bottom surface 38 of the top plate 14. Specifically, FIG. 4 depicts that the bottom surface of 38 is recessed from the top of the top plate 14 and extends into the chamber defined by the top plate 14 and the side wall 28. Additionally, FIG. 4 depicts that each of the channels 32 extends all the way through the top plate 14 to define a plurality of openings in the bottom surface 38. FIG. 4 depicts that the catch wall 40 is formed into the side wall 28 of one end of the top plate 14, however, it will be understood that a similar catch wall 40 is formed in the other sidewall of the cassette. As shown in FIG. 4 the catch wall 40 is centrally located and extends for a portion of the end of the side wall 28. The end of the side wall 28 in which the catch wall 40 is located is, in the depicted embodiment, offset from the rest of the side wall 28. Specifically, the side wall 28 steps inward toward the recessed bottom surface 38 as the wall 28 extends towards the catch wall 40. This is understood to provide one end of the top plate 14 with a reduced width. This reduced width feature can be employed for orientation purposes, and specifically to allow the narrowed end of the top plate 14 to be received within a device for fracturing the top plate 14. Such a device will be described in greater detail hereinafter.

Figure 5:
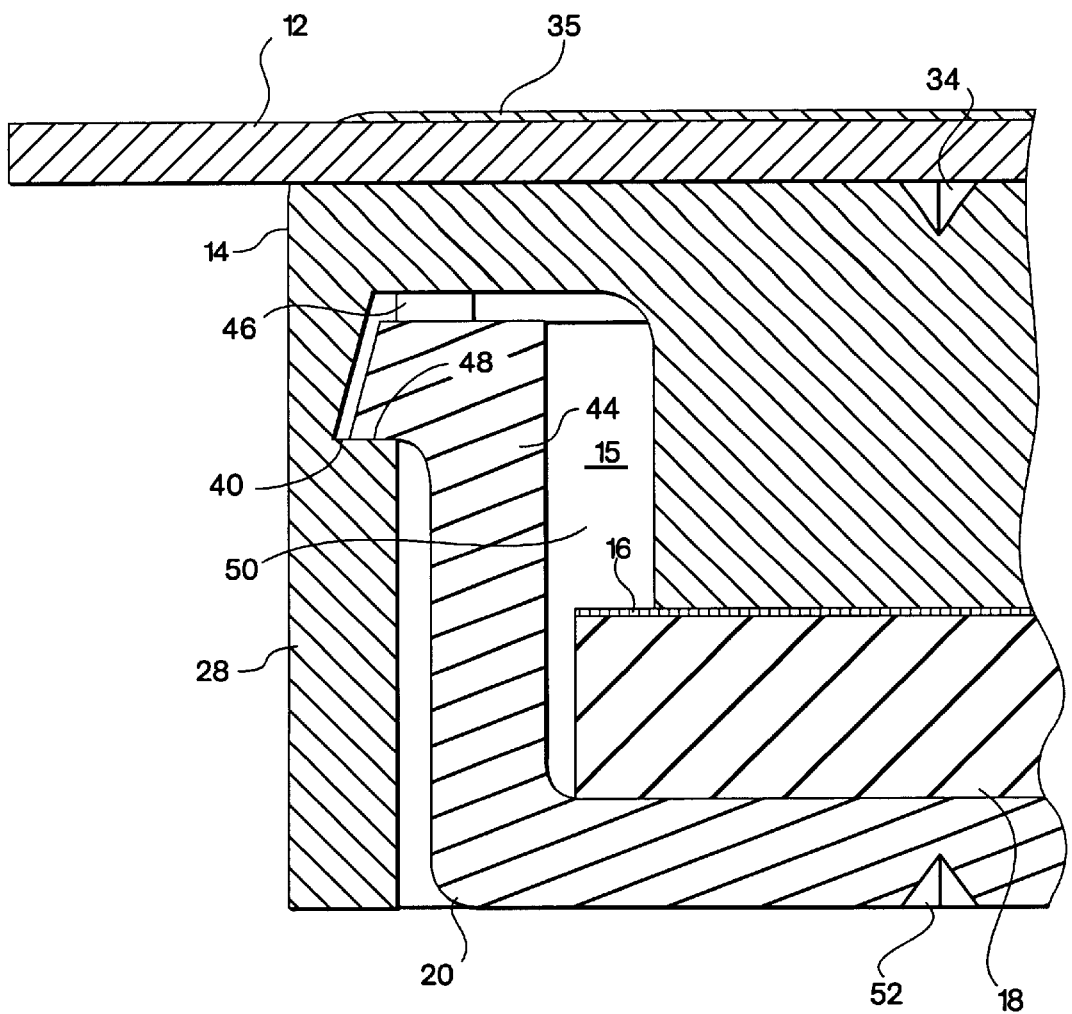
FIG. 5 depicts in greater detail the latching mechanism of the assay cassette of FIG. 1.

FIG. 5 depicts in greater detail the engagement mechanism of the cassette assembly 10. Specifically FIG. 5 provides a cross-sectional view of the cassette assembly, showing the engagement mechanism that is formed by the catch wall 40 located in the end wall 28 of the top plate 14 and by the lock wall 44 located on the end wall of the bottom plate 20. The locking wall 44 includes a lip 48 that extends outwardly from the side wall of the bottom plate 20. The lip 48 can fit into the chamber defined by the catch wall 40 that is notched into the side wall 28 of the top plate 14. Upon insertion of the locking wall 44 into the cavity formed above the catch wall 40, the lip 48 extends into the cavity and butts against the catch wall 40, which acts as a mechanical stop preventing the lip 48 from moving downwardly. Above the lip 48, is a gap 46 that allows the top plate 14 to travel downward toward the bottom plate 20 and compress the membrane 16 held between the top plate and the bottom plate. Accordingly, upon insertion of the locking wall 44 into the cavity formed above the catch wall 40, the bottom plate 20 is stopped from moving downwardly and away from the top plate, thereby being engaged therewith, however, the top plate 14 can be move downward toward the bottom plate 20 to allow further compression of the membrane 16. Such movement can occur when the assay cassette 10 is placed within a container, such as that described hereinafter with reference to FIG. 8, and the top plate of the container is brought down and pushed against the top plate 14 of the assay cassette.

Although the assay cassette 10 has been depicted having the locking walls 48 and catch wall 40 as the engaging mechanism, it will be understood that other devices can be employed for engaging the top plate 14 with the bottom plate 20. For example, a clasp mechanism can be employed which can wrap around the exterior of the assay cassette 10, wrapping around both the top plate 14 and the bottom plate 20 and thereby preventing the plates from separating. Similarly, a screw mechanism can be employed for allowing a screw to be threaded through both the top plate 14 and the bottom plate 20, thereby joining the two plates together. Gaskets can be applied around the periphery of the plate, to allow the plates to seal and to allow further compression of the plates, and the membrane Additionally, other techniques can be employed, such as ultra-sonic welding, fast drying glues and adhesives, which can be applied in various ways for permanently joining the top plate 14 to the bottom plate 20, and other mechanisms can be employed for allowing the plates to be brought closer together and for allowing the membrane 16 to be compressed.

FIG. 5 further depicts the membrane 16, and filter pad 18, which are disposed between the top plate 14 and the bottom plate 20. In particular, FIG. 5 shows the filter pad 18 supports the membrane 16, and provides a raised surface upon which the membrane 16 can be seated. FIG. 5 further depicts that the coupling of the bottom plate 20 with the top plate 14 forms an interior chamber 15 in which are disposed the membrane 16 and the filter pad 18. The filter pad 18 is dimensionally adapted to raise the membrane 16 into engagement with the recessed bottom surface 38 of the top plate 14 when the top plate 14 is joined to the bottom plate 20. In this way, the membrane 16 is sandwiched within the assay cassette 10.

The membrane 16 can be a nitrocellulose membrane bearing electrophoretically resolved antigens of *Borrelia burgdorferi* was prepared by standard blotting procedures (e.g., Towbin, H., Stehelin, T. and Gordon, J., *Proc. Nat. Acad. Sci. U.S.A.* 76:4350–4354 (1979)), then washed 30 minutes in distilled water. Additional stripes of defined antigens may be applied to the membrane at this point by non-electrophoretic methods. The nitrocellulose membrane can have a 0.2$\mu$ pore size and can be obtained from commercial suppliers such as Schleicher & Schuell (Keene, N.H.), Whatman, Inc. (Fairfield, N.J.), or others. The nitrocellulose membrane can be cut to fit the cassette, such as being cut to 2" wide ×4" long. The wet membrane can be placed over an identically sized piece of dry filter paper. A variety of filter papers may be used, but a paper specifically intended for wicking is optimal, such as. #320 paper from Ahlstrom Filtration Inc. (Mount Holly Springs, Pa. ), a 2.5 mm thick blotting paper.

It will further be noted that in the embodiment depicted in FIG. 5, the bottom 20 includes a weakened portion 52 that, when the top plate 14 is joined to the bottom plate 20 is positioned in opposition to the frangible portion 34 of top plate 14. This alternate embodiment allows a shear force to fracture the top plate 14 and the bottom plate 20.

Figure 6:
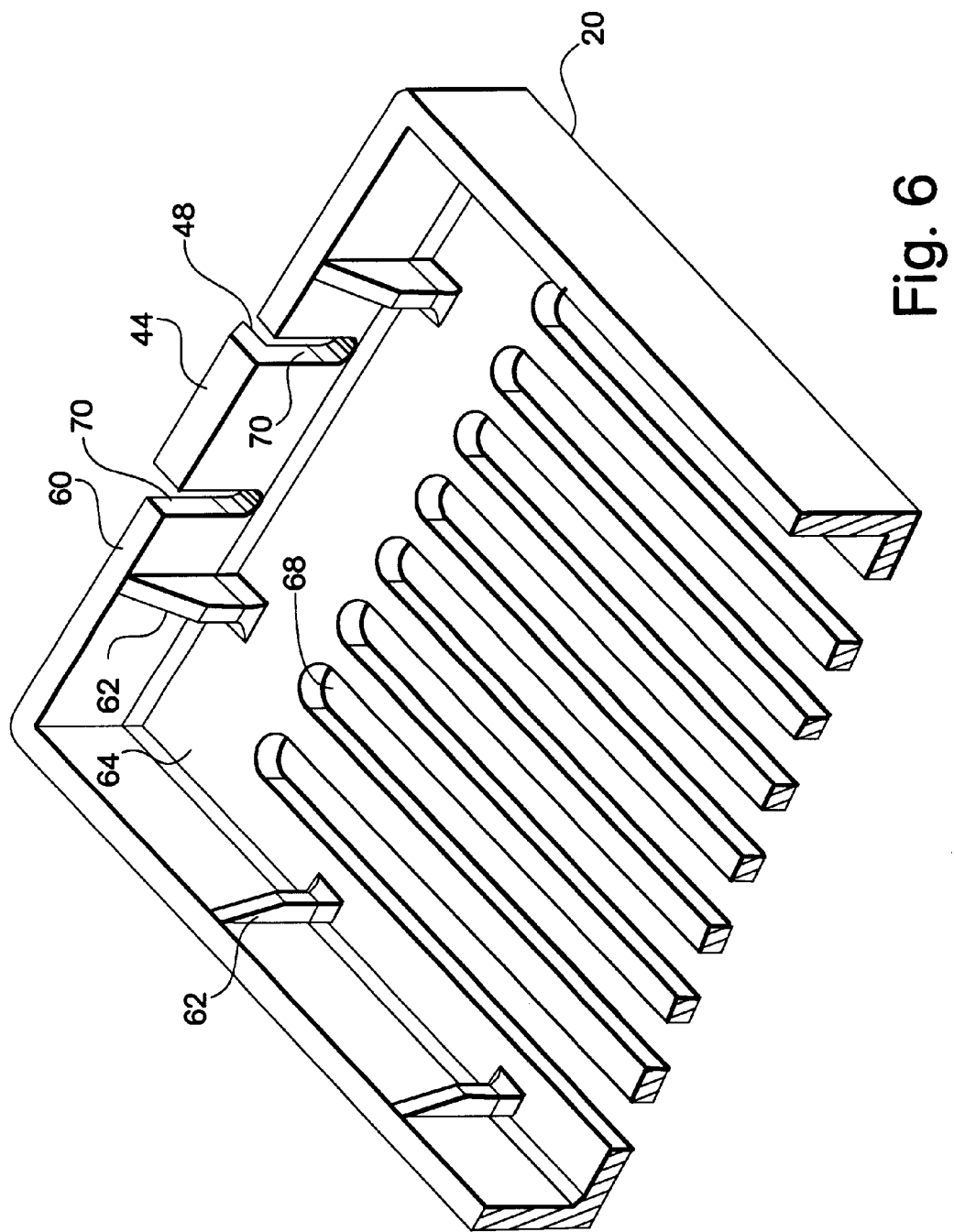
FIG. 6 depicts in greater detail the bottom plate of the assay cassette.

FIG. 6 depicts in greater detail the bottom plate 20. Specifically, FIG. 6 depicts the bottom plate 20, the side wall 60, alignment pins 62, bottom surface 64, vacuum slots 68, and the locking wall 44.

The side wall 60 forms a peripheral wall around the bottom plate 20, running along the full perimeter of the bottom surface 64. Along the internal surface of the side wall 60 are a plurality of alignment pins 62. The alignment pins 62 are mounted to the side wall and dimensionally adapted to extend into the interior of the bottom plate 20 a distance sufficient to allow for proper alignment of the filter pad 18 and filter 16 that are disposed within the bottom plate 20. FIG. 6 further depicts the locking wall 44 that is formed integrally into one part of side wall 60. Specifically, the depicted locking wall 44 is formed by two groves 70 that extend through the side wall 60. Accordingly, the locking wall 44 lacks side wall support and is anchored only at the bottom section of locking wall 44. Accordingly, as the material of the bottom plate 20 is a somewhat resilient molde or machined plastic material, the side wall 44 can deflect laterally, either inwardly or outwardly relative to the interior of the bottom plate 20. FIG. 6 further depicts that the locking wall 44 has a outwardly extending protrusion that forms the lip 48. This outwardly extending protrusion causes the locking wall 44 to deflect inwardly as the bottom plate is being slid into the top plate. However, upon reaching the cavity above the catch wall 40, the resilient locking wall 44 drives the protrusion into the cavity causing the lip 48 to butt against the locking wall 40 engaging the bottom plate with the top plate.

Figure 7:
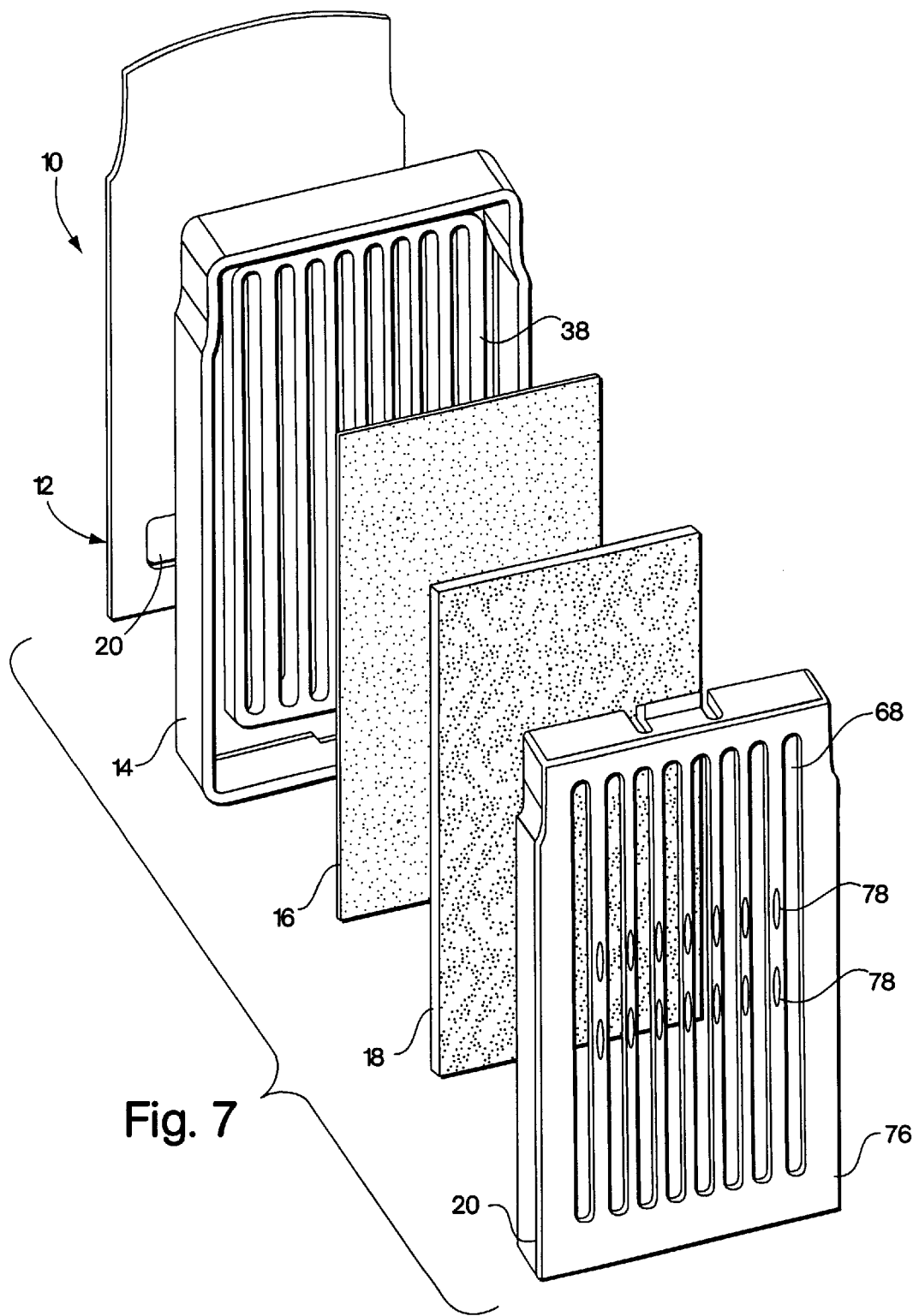
FIG. 7 provides an exploded view of the assay cassette of FIG. 1.

FIG. 7 provides an exploded view with an upward looking prospective of the assay cassette 10 depicted in FIG. 1. Specifically, FIG. 7 shows the assay cassette 10 which includes the label 12, the top plate 14, the membrane 16, the filter pad 18 and the bottom plate 20. From the prospective provided by FIG. 7 it can be seen that the recessed bottom surface 38 of the top plate 14 is brought down upon the membrane 16 to sandwich the membrane 16 and filter pad 18 between the recessed bottom surface 38 and the bottom plate 20.

FIG. 7 also illustrates the bumps 78 that are optionally provided on the bottom surface 76 of the bottom plate 20. Specifically, the bumps 78 are located on the ribs 36 between the channels 68 that extend through the bottom plate 20. The bumps 78 on the ribs 36 help push the filter pad 18 against the bottom surface of the top plate 14, by allowing the vacuum applied to the underside of the cassette to act on the cassette and pull down the membrane and filter pad. In the depicted embodiment there are two sets of bumps 78, however, any suitable number and pattern can be employed to provide for optimal pressure on the filter pad. The depicted bumps 78 include an upper set and a lower set, each of which is longitudinally spaced apart. Together the pairs of bumps provide a gap between the bottom surface 76 of the cassette 10 and the bottom surface of the chamber in which the cassette 10 can be received during a rapid flow through assay. One such chamber is described in the above referenced patent application entitled "Systems and Method for Rapid Blot Screening", and another chamber is described with reference to FIG. 8. The gap provided by the bumps 78 allows for a negative pressure within the interior of the chamber holding the assay cassette 10 to be applied through the grooves 68 to the underside of the filter pad 18 and membrane 16. In this way, a negative pressure applied to the chamber holding the assay cassette 10 can act on a sample material applied through the sample window 20 in label 12 to pull sample material through the membrane 16 and filter pad 18 and to be drawn through the grooves 68.

Figure 8:
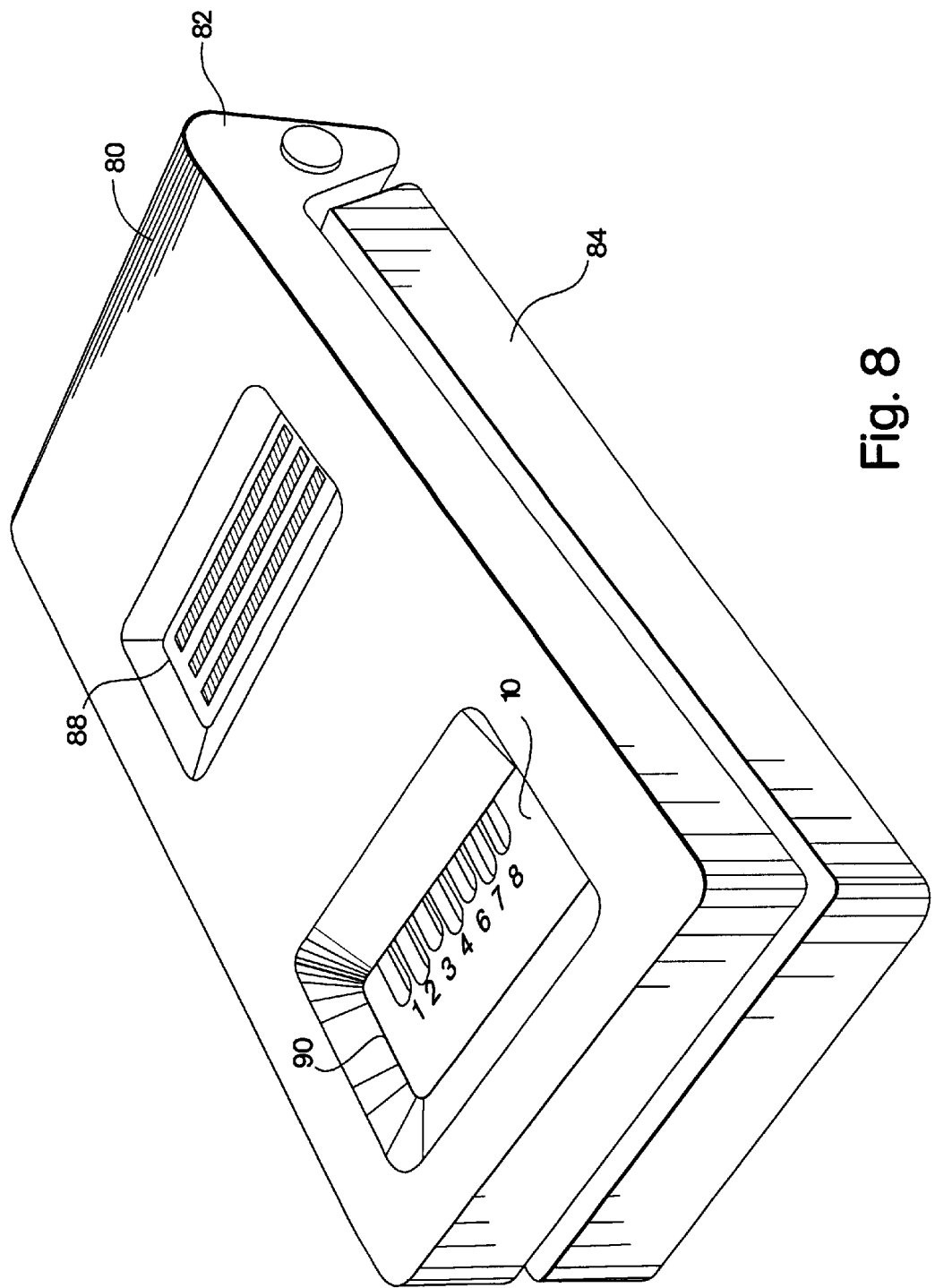
FIG. 8 illustrates a chamber for holding an assay cassette during an assay such as a rapid flow-through assay.

One such chamber for holding the assay cassette 10 is depicted in FIG. 8. Specifically FIG. 8 illustrates a chamber 80 that includes a lid 82 that is hingedly mounted to a base plate 84, and then further includes a label window 88 and a pipette window 90. As illustrated by FIG. 8 the assay cassette 10 can be received within the chamber 80 to be held there during the rapid flow through assay. The lid 82 can seal against the base plate 84, wherein the base plate 84 can have a perimeter gasket that allows a vacuum seal to be formed between the lid 80 and the base plate 84. Similarly a gasket seal can fit above the perimeters of the underside of the label viewing window 88 and the pipette window 90. This allows the lid 80 to form vacuum seals against the assay cassette 10, while still allowing a lab technician to view the label on the assay cassette 10 and to access the channels of the assay cassette 10. In an alternative embodiment, each of the windows comprises a transparent surface located within the body of the lid 80. The transparent servers provides a viewing structure that allows for viewing of the label 12, and for viewing of the channels of the assay cassette 10. In other embodiments of the chamber 80, no viewing windows are provided. The chamber 80 can further include a vacuum port (not shown) that can be disposed in the bottom plate 84 and that can be employed for applying a negative pressure to the interior of the chamber 80. As discussed above with a reference FIG. 7 this negative pressure can draw sample and other fluid material through the membrane 16 for performing the flow through assay.

In one embodiment, the base plate 84 includes a perimeter gasket against which an assay cassette received within the chamber 80 can sit. The gasket provides a vacuum seal that forms above the perimeter of the bottom surface 76 of the bottom plate 20 of the assay cassette 10. A vacuum port (not shown) in the bottom surface of the bottom plate 84 can be aligned to apply a negative pressure against the bottom surface 76 of the assay cassette 10. The chamber gasket seal between the assay cassette 10 and the bottom plate 84 of the container 80 provides a vacuum tight chamber that can maintain the negative pressure so that it is transmitted to the sample material being processed in the assay cassette 10.

Figure 9:
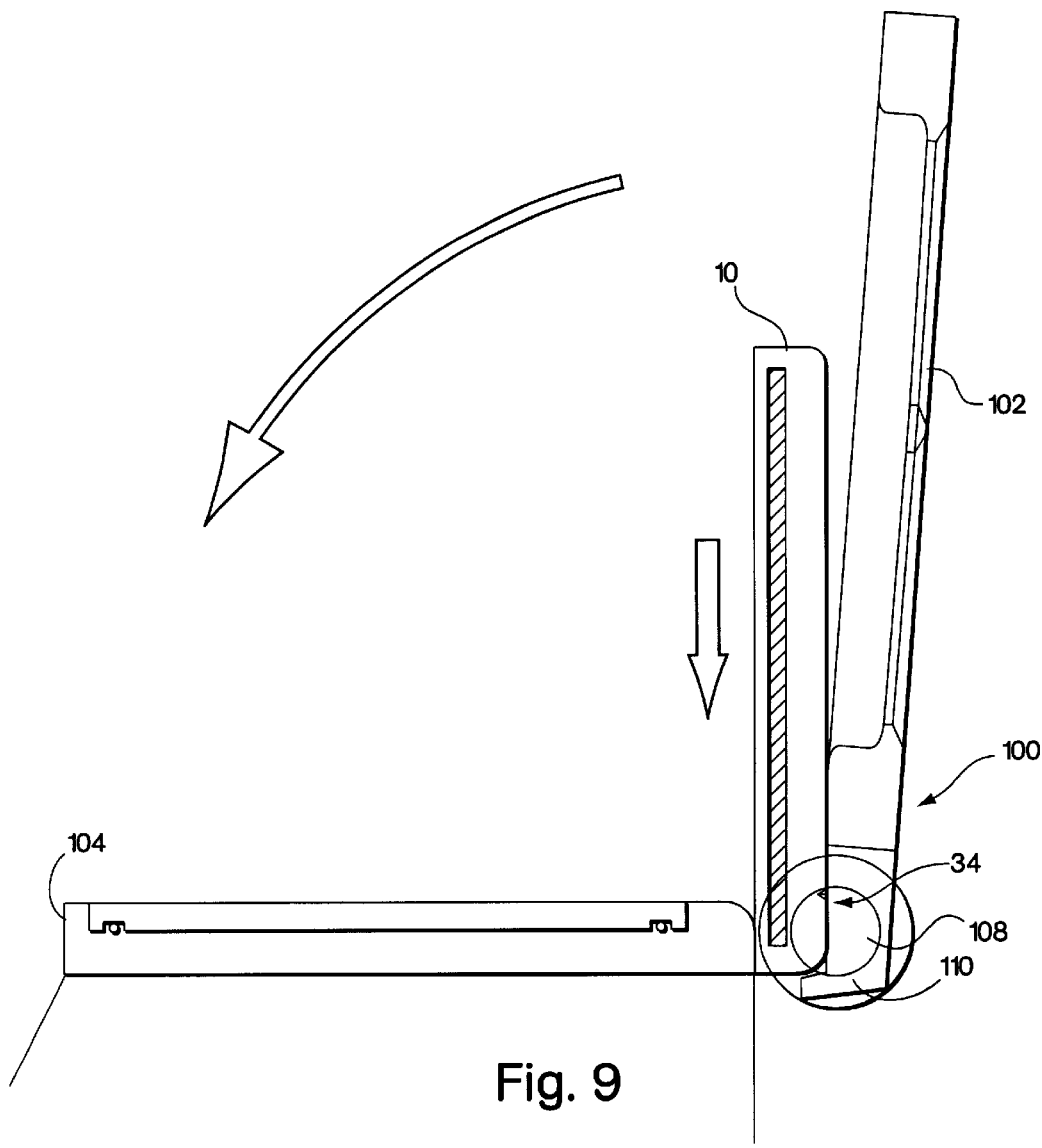
FIG. 9 illustrates one system for opening the assay cassette of FIG. 1.

After the assay cassette 10 has been processed such that sample material has been filtered through the membrane 16 held by the assay cassette 10, the assay cassette 10 can be opened to allow a lab technician to remove the membrane 16 for subsequent processing and analysis. To this end, the cassette 10 can be placed in an opening device, such as the device 100 depicted in FIG. 9. As shown in FIG. 9 the device 100 can include an upper plate 102 that is hingedly mounted to a lower plate 104, by the hinge 108. For the illustrated embodiment, the upper plate 102 is spaced away from the base plate 104 a distance sufficient to allow the assay cassette 10 to fit within the gap formed between the two plates. For the depicted embodiment the assay cassette 10 fits within the gap and comes to rest against the arm 110 that acts as a stop to prevent further movement of the assay cassette 10. The arm 110 is disposed on the upper plate 102 a distance sufficient to dispose the frangible portion 34 at a point at which sheer forces will act when the upper plate 102 is pivoted downwardly toward the base plate 104.

Figure 10:
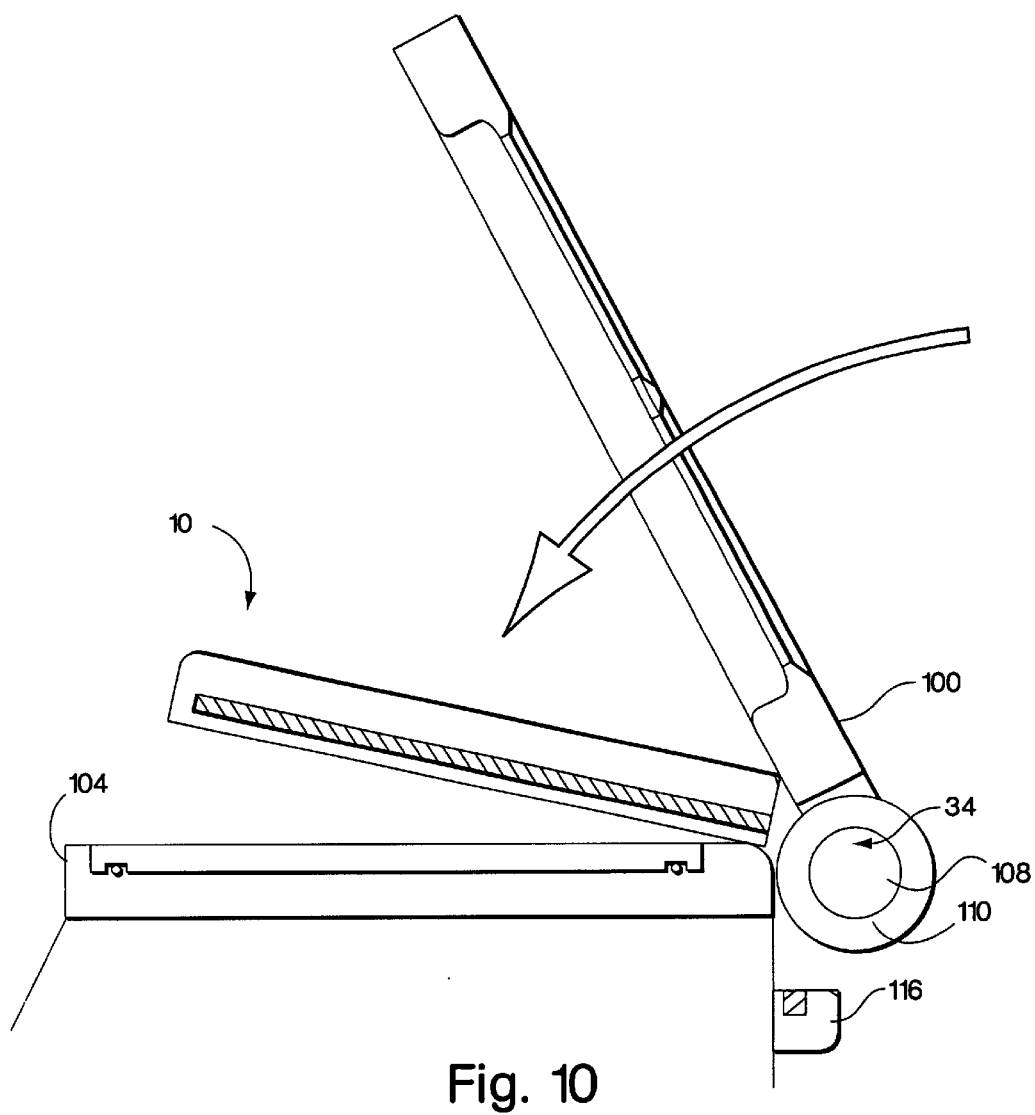
FIG. 10 illustrates the cassette being opened by the device of FIG. 1.

As shown by FIG. 10 pivoting the upper plate 102 toward the base plate 104 causes sheer forces to act on the frangible portion 34 allowing the one end of the assay cassette 10 to break off from the other end. In the embodiment depicted in FIG. 10 the portion of the assay cassette 10 that breaks off 116 is allowed to fall away from the device 100 and can land into a container, such as a jelly container, that can be adapted for collecting waste product that can be disposed of properly later. In the depicted practice, the entire end of the cassette is separated from the cassette, although in other embodiments, only a portion of the top section is removed.

Figure 11:
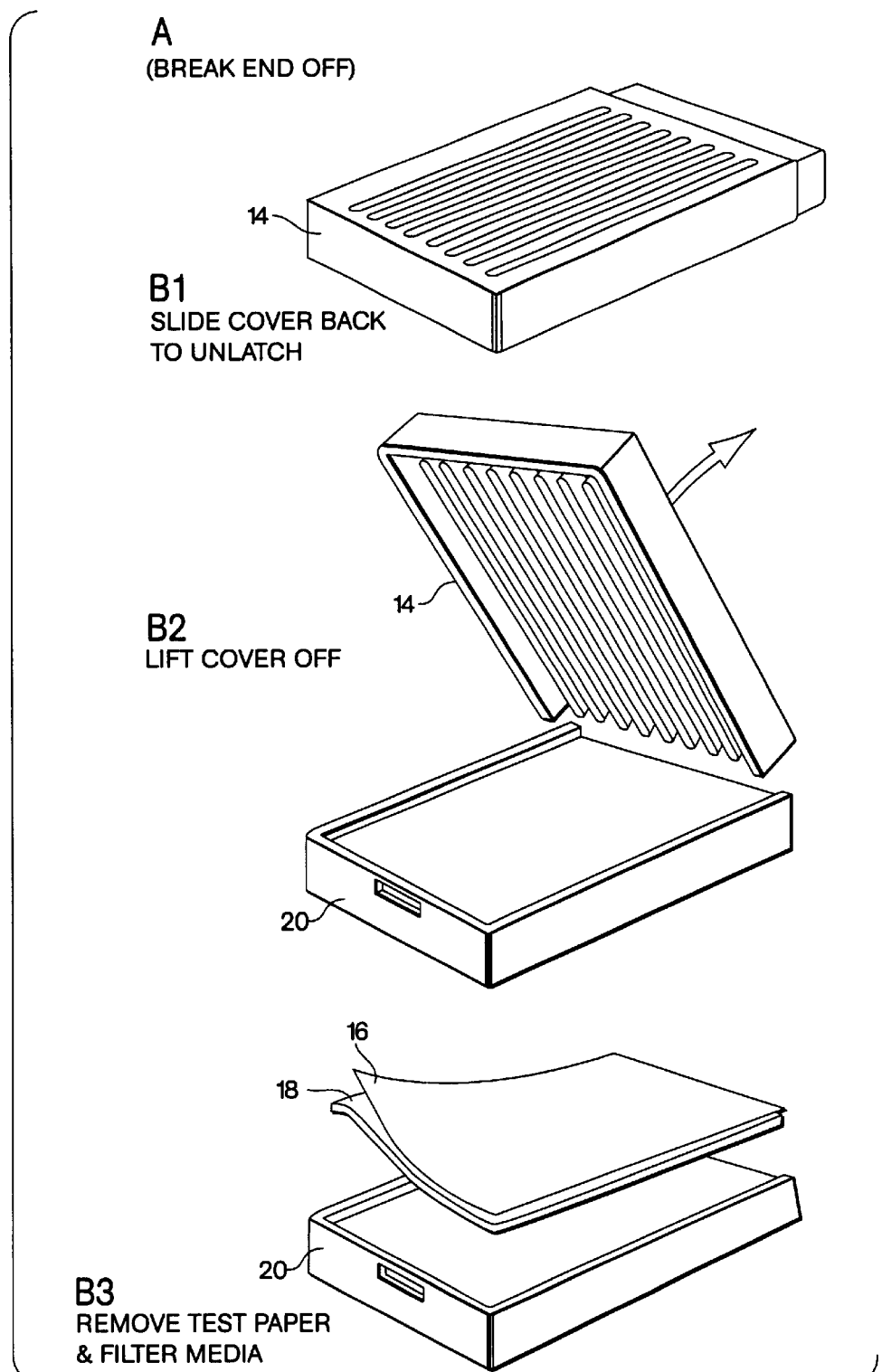
FIG. 11 illustrates the removal of the filter of an assay cassette that has been opened.

FIG. 11 depicts that once the end portion of the assay cassette 10 is fractured and removed from the larger component of the assay cassette 10, the filter paper can be removed from the interior chamber. To this end FIG. 11 shows that the top plate 14 can be slid back to unlatch the top plate 14 from the bottom plate 20. In a subsequent step the lab technician can lift the top plate 14 from the bottom plate 20 exposing the membrane 16. Any additional steps that are necessary can be performed at that time and after performing such steps the lab technician can remove the membrane 16 and filter medium 18 from the bottom plate 20 for further analysis or for disposal.

Those skilled in the art will know or be able to ascertain using no more than routine experimentation, many equivalents to the embodiments and practices described herein. It will also be understood that the systems described herein provide advantages over the prior art including improved ease of processing. Accordingly, it will be understood that the invention is not to be limited to the embodiments disclosed herein, but is to be understood from the following claims, which are to be interpreted as broadly as allowed under the law.

We claim:

1. An assay cassette for use in a flow-through assay, comprising
   a top plate having a frangible portion extending transversely across said top plate, and
   a bottom plate having a peripheral sidewall and being adapted to couple with said top plate to define an interior chamber capable of receiving a membrane,
   wherein said top plate includes a recessed bottom surface for extending into said chamber a distance sufficient to but against a membrane received therein.

2. An assay cassette according to claim 1, wherein said frangible portion includes a score.

3. An assay cassette according to claim 1, wherein said frangible portion includes a hinge.

4. An assay cassette according to claim 1, further including a substantially open channel extending through said top plate, to provide an opening through said top plate and to allow contact with a membrane within said chamber.

5. An assay cassette according to claim 1, further including a plurality of open channels formed in a pattern and extending through said top plate.

6. An assay cassette according to claim 1, further comprising a plurality of open channels extending longitudinally across said top plate.

7. An assay cassette according to claim 6, wherein said engagement mechanism includes a catch wall for holding said top plate together with said bottom plate.

8. An assay cassette according to claim 1, further comprising an engagement mechanism for holding said top plate together with said bottom plate.

9. An assay cassette according to claim 1, further including a vacuum port disposed in said bottom plate.

10. An assay cassette according to claim 1, further including a plurality of open channels extending longitudinally across said bottom plate for providing a plurality of channels through said bottom plate.

11. An assay cassette, comprising
    a top plate having a channel extending therethrough,
    a bottom plate for joining to said top plate, and
    an engagement mechanism for joining said top plate with said bottom plate and for allowing said top plate to move toward a membrane seated between said top plate and said bottom plate to cause said channel to press against said membrane and to form on the filter a substantially fluid-tight seal around a portion of said filter enclosed by said channel;
    wherein at least one of said top plate and said bottom plate includes a frangible section for allowing the respective plate to be divided.

12. An assay cassette according to claim 11, further comprising a vacuum port.

13. An assay cassette according to claim 11, wherein said bottom plate includes a vacuum port for applying a negative pressure to one side of a filter seated between said top plate and said bottom plate.

14. An assay cassette according to claim 13, wherein said vacuum port comprises a channel extending through said bottom plate.

15. An assay cassette according to claim 11, wherein said top plate includes a plurality of channels for forming a plurality of substantially fluid-tight seals on the filter maintained between the top plate and the bottom plate.

16. A method of manufacturing an assay cassette, comprising
    providing a top plate and a bottom plate capable of being fitted together to define an interior chamber suitable for receiving a filter membrane, wherein said top plate includes a recessed bottom surface for extending into said chamber a distance sufficient to but against said filter membrane, and
    forming on said at least one of said top plate and bottom plate a frangible section for allowing said respective plate to be divided into two or more components.

* * * * *

UNITED STATES PATENT AND TRADEMARK OFFICE
CERTIFICATE OF CORRECTION

PATENT NO. : 6,303,389 B1
DATED : October 29, 2001
INVENTOR(S) : Andrew E. Levin and William Bowers It is certified that error appears in the above-identified patent and that said Letters Patent is hereby corrected as shown below:

<u>Title page, Item [54] and Column 1, line 2,</u>
Title, please delete "THEREFOR"

<u>Title page,</u>
Item [75], Inventors, please delete "Cambridge" and substitute -- Peabody --.
Item [63], Related U.S. Application Data, before "application No. 08/884,018", please delete "in-part".

Signed and Sealed this

Eighth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.     : 6,303,389 B1
DATED          : October 16, 2001
INVENTOR(S)    : Andrew E. Levin and William Bowers It is certified that error appears in the above-identified patent and that said Letters Patent is hereby corrected as shown below:

<u>Title page, Item [54] and Column 1, line 2,</u>
Title, please delete "THEREFOR"

<u>Title page,</u>
Item [75], Inventors, please delete "Cambridge" and substitute -- Peabody --.
Item [63], Related U.S. Application Data, before "application No. 08/884,018", please delete "in-part".

This certificate supersedes Certificate of Correction issued June 8, 2004.

Signed and Sealed this

Nineteenth Day of July, 2005

JON W. DUDAS
*Director of the United States Patent and Trademark Office*